(12) United States Patent
Abeytunge et al.

(10) Patent No.: US 9,797,816 B2
(45) Date of Patent: Oct. 24, 2017

(54) DEVICES APPLICABLE TO TISSUE(S) WHICH FACILITATES CONFOCAL MICROSCOPY, OPTICAL MICROSCOPY, SPECTROSCOPY AND/OR IMAGING

(71) Applicant: MEMORIAL SLOAN-KETTERING CANCER CENTER, New York, NY (US)

(72) Inventors: Sanjee Abeytunge, Brooklyn, NY (US); Ricardo Toledeo-Crow, New York, NY (US); Milind Rajadhyaksha, New York, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 0 days.

(21) Appl. No.: 14/421,506

(22) PCT Filed: Aug. 13, 2013

(86) PCT No.: PCT/US2013/054653
§ 371 (c)(1),
(2) Date: Feb. 13, 2015

(87) PCT Pub. No.: WO2014/028439
PCT Pub. Date: Feb. 20, 2014

(65) Prior Publication Data
US 2015/0233798 A1    Aug. 20, 2015

Related U.S. Application Data

(60) Provisional application No. 61/682,407, filed on Aug. 13, 2012.

(51) Int. Cl.
*G01N 1/28* (2006.01)

(52) U.S. Cl.
CPC .................................. *G01N 1/286* (2013.01)

(58) Field of Classification Search
CPC ............................................... G01N 1/023
See application file for complete search history.

(56) References Cited

U.S. PATENT DOCUMENTS

| 3,446,635 A | * | 5/1969 | Kwiat | ..................... A23L 3/44 |
| | | | | 34/305 |
| 5,978,695 A | * | 11/1999 | Greenwald | ............ G02B 21/34 |
| | | | | 600/407 |

(Continued)

FOREIGN PATENT DOCUMENTS

| CN | 101806955 A | 8/2010 |
| JP | H07-234179 A | 9/1995 |

(Continued)

OTHER PUBLICATIONS

International Search Report for International Application No. PCT/US2013/054653 dated Nov. 28, 2013.

(Continued)

*Primary Examiner* — Sally Merkling
(74) *Attorney, Agent, or Firm* — Andrews Kurth Kenyon LLP

(57) ABSTRACT

Exemplary embodiments of apparatus and method for facilitating an analysis of a sample(s) can be provided. For example, using a first arrangement(s), it can be possible to receive the sample(s) thereon. Further, for example, using a second arrangement(s), it can be possible to cause a force to be applied on a portion(s) of the sample(s) such that a surface(s) of the sample(s) can be flattened against a section(s) of the first arrangement(s).

23 Claims, 28 Drawing Sheets

(56) References Cited

U.S. PATENT DOCUMENTS

| | | | |
|---|---|---|---|
| 7,227,630 B1 * | 6/2007 | Zavislan | G02B 21/0028 356/244 |
| 2002/0122236 A1 | 9/2002 | Fisher et al. | |
| 2003/0181801 A1 * | 9/2003 | Lasser | A61B 6/0414 600/407 |
| 2007/0161051 A1 | 7/2007 | Tsinberg | |

FOREIGN PATENT DOCUMENTS

| | | |
|---|---|---|
| JP | 2000035392 A1 | 2/2000 |
| RU | 2031406 | 3/1995 |
| RU | 2031406 C1 | 3/1995 |
| WO | WO 00/49392 A1 | 8/2000 |

OTHER PUBLICATIONS

International Written Opinion for International Application No. PCT/US2013/054653 dated Nov. 28, 2013.
Supplementary European Search Report for European Patent Application No. 13829611 dated Jun. 23, 2016.
First Australian Patent Examination Report for Australia Patent Application No. 2013302839 dated Sep. 24, 2016.

* cited by examiner

DEVICES APPLICABLE TO TISSUE(S) WHICH FACILITATES CONFOCAL MICROSCOPY, OPTICAL MICROSCOPY, SPECTROSCOPY AND/OR IMAGING

CROSS-REFERENCE TO RELATED APPLICATIONS

This present application relates to and claims priority from International Patent Application No. PCT/US2013/054653 filed Aug. 13, 2013, and from U.S. Patent Application No. 61/682,407, filed on Aug. 13, 2012, the entire disclosures of which are incorporated herein by reference.

STATEMENT OF FEDERAL SUPPORT

The present disclosure was made with U.S. Government support under grant numbers R01EB002715 and R01 EB012466 from the National Institute of Health. Thus, the Government has certain rights to the disclosure described and claimed herein.

FIELD OF THE DISCLOSURE

Exemplary embodiments of the present disclosure relate to imaging and application of microscopy to anatomical structures, and more particular to devices applicable to any type of tissue(s) which can facilitate confocal microscopy, optical microscopy and/or imaging.

BACKGROUND INFORMATION

A complete and accurate surgical excision of cancers, while preserving as much of the surrounding normal tissue as intact as possible, can be guided by the examination of pathology for residual cancer margins. However, a preparation of the pathology can be labor-intensive, and can be time-consuming. The processing of excised tissue and preparation of thin sections for pathology can take hours (e.g., for frozen sections) or days (e.g., for fixed sections), which can result in insufficient sampling of tissue, and inaccurate and/or incomplete removal of cancer. Consequently, a large number (e.g., between about 20% and 70%, depending on the setting) of patients undergo re-excision (e.g., repeat surgery) and/or chemotherapy and/or radiotherapy.

Confocal microscopy can image nuclear and cellular morphology in living tissues, either in vivo or in freshly excised, or biopsied, tissue ex vivo, without the need for processing tissue or preparation of thin sections. A detection of residual cancer margins can be made possible in fresh tissue within minutes. Rapid mosaicking, for example, acquisition and stitching together of a large number of images, can facilitate imaging over large areas.

Accordingly, there may be a need to address and/or overcome at least some of the above-described deficiencies and limitations, and to provide exemplary embodiments of devices according to the present disclosure as described in further details herein.

SUMMARY OF EXEMPLARY EMBODIMENTS OF THE DISCLOSURE

Indeed, one of the objects of certain exemplary embodiments of the present disclosure can be to address the exemplary problems described herein above, and/or to overcome the exemplary deficiencies commonly associated with the prior art as, for example, described herein. Accordingly, for example, provided and described herein are certain exemplary embodiments of exemplary devices according to the present disclosure which can be applicable to tissue(s) which facilitates confocal microscopy, optical microscopy and/or imaging.

Due to the three-dimensional ("3D") topography and irregular shapes and sizes of fresh surgically excised, or biopsied, tissue, mounting the tissue for imaging large areas with a scanning confocal microscope, or other modalities, as mentioned above, can be challenging due to the following problems:

a. Sag, for example, bending of the desired tissue surface (e.g., imaging plane) to be imaged.
b. Tissue stability during imaging and mosaicing procedures.
c. Uniform tissue flatness for the surface to be imaged.
d. Constant hydration of tissue since it is fresh and living.
e. Orthogonality of the desired tissue surface (e.g., imaging plane) relative to optic axis of objective, for example, desired tissue surface to be imaged must be parallel to the "object plane" of the microscope.

Confocal mosaicing microscopy, and possibly other emerging/competing optical imaging modalities, such as optical coherence tomography, multiphoton microscopy, etc. can facilitate technologies for rapid pathology at the bedside in large amounts of fresh tissue. One of the important factors to image a large area of the fresh tissue can be that the entire imaging surface should be parallel to the imaging plane.

According to an exemplary embodiment of the present disclosure, it can be preferable to provide a technology platform, which can be called "confocal mosaicing microscopy," to facilitate a rapid pathology at the bedside. According to such exemplary embodiment, it can be beneficial to mount surgically-excised tissue in a microscope. A device according to a certain exemplary embodiment of the present disclosure can be provided for mounting fresh tissue from surgery. While the exemplary embodiment described herein can be directed to the use of a fresh tissue from surgical excisions for use in surgical settings, such exemplary device can also be used for biopsies in clinical settings.

For example, with respect to a diverse range of tissues (e.g., skin, breast, head-and-neck or otolaryngologic, urologic, brain or neurologic, etc.) and wide range of settings sizes and shapes (e.g., large excisions, thin excisions, shave biopsies, punch biopsies, needle core biopsies, fine needle aspirations, etc.), it can be possible to utilize and/or apply exemplary embodiments of such device to various targets and/or tissues. Further, the exemplary embodiments of the device, according to the present disclosure, can also be used with other present and future optical imaging modalities, such as optical coherence tomography, reflectography, scanning electrochemical microscopy, multiphoton microscopy, etc.

These and other objects of the present disclosure can be achieved by provision of an exemplary apparatus for facilitating an analysis a sample(s), which can include a first arrangement(s) which can be configured to receive the sample(s) thereon, and a second arrangement which can be configured to apply a force on a portion(s) of the sample(s) such that a surface(s) of the sample(s) can be flattened against a section(s) of the first arrangement(s). The second arrangement(s) can be configured to apply the force to an area of the portion(s) that can be located on a further surface that can be approximately opposite to the surface(s). The second arrangement(s) can include an inflatable arrangement(s), a piston(s), a cassette lid(s), and/or a plurality of pins. The second arrangement(s) can also include a flexible tissue holding arrangement(s) and a vacuum arrangement(s). The flexible tissue holding arrangement(s) can include a silicon bag(s).

In some exemplary embodiments of the present disclosure, a third arrangement can be configured to directly or indirectly secure the sample(s) in a position to maintain the surface(s) in a flat manner against the section(s). A fourth arrangement(s) can be configured to obtain data regarding a portion(s) of the sample(s) from below the flattened surface(s). The fourth arrangement can include a microscope arrangement, and the data can include image information regarding the portion(s) of the sample(s).

In another embodiment of the present disclosure can be a method for facilitating an analysis of a sample(s), which can include providing an arrangement(s) so as to receive the sample(s) thereon, providing the sample(s) on the arrangement(s), and causing a force to be applied on a portion(s) of the sample(s) such that a surface(s) of the sample(s) can be flattened against a section(s) of the arrangement(s). The force can be applied using a further arrangement(s), which can include an inflatable arrangement(s). The further arrangement(s) can include an inflatable arrangement holder(s) and a piston(s). The inflatable arrangement(s) can be inflated, and the piston(s) can be screwed into the inflatable arrangement holder(s) to cause the inflatable arrangement(s) to apply the force to the sample(s). In some exemplary embodiments of the present disclosure, the further arrangement can include a cassette lid(s). The inflatable arrangement(s) can be inflated, and the cassette lid(s) can be closed to cause the inflatable arrangement(s) to apply the force to the sample(s). The further arrangement(s) can include a plurality of pins.

In certain exemplary embodiments of the present disclosure, the further arrangement(s) can includes a flexible tissue holding arrangement(s) and a vacuum arrangement(s). The sample(s) can be placed in the flexible tissue holding arrangement(s), and the air can be vacuumed from the flexible tissue holding arrangement(s) using the vacuum(s) to apply the flexible tissue holding arrangement(s). The flexible tissue holding arrangement(s) can include a silicon bag(s).

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

For a more complete understanding of the present disclosure and its advantages, reference is now made to the following description, taken in conjunction with the accompanying drawings, in which.

Figure 1:
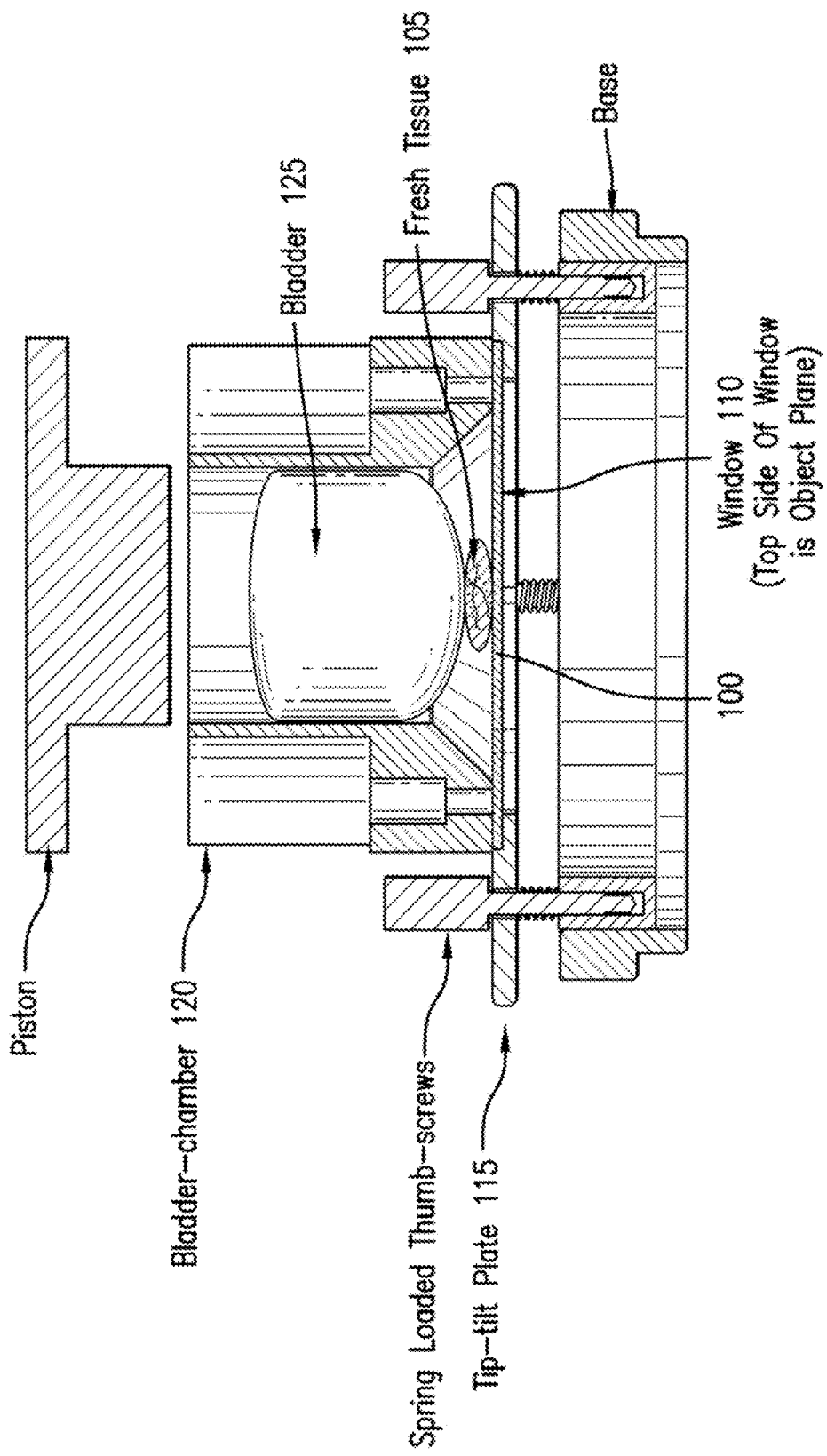
FIG. 1 is a side cross-sectional view of an exemplary tissue-mounting device for fresh tissue, with no force applied to a bladder, in accordance with a first exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments and is not limited by the particular embodiments illustrated in the figures and the accompanying claims. It is intended that changes and modifications can be made to the described embodiments without departing from the true scope and spirit of the subject disclosure and the accompanying claims.

DETAILED DESCRIPTION OF EXEMPLARY EMBODIMENTS

Figure 12A:
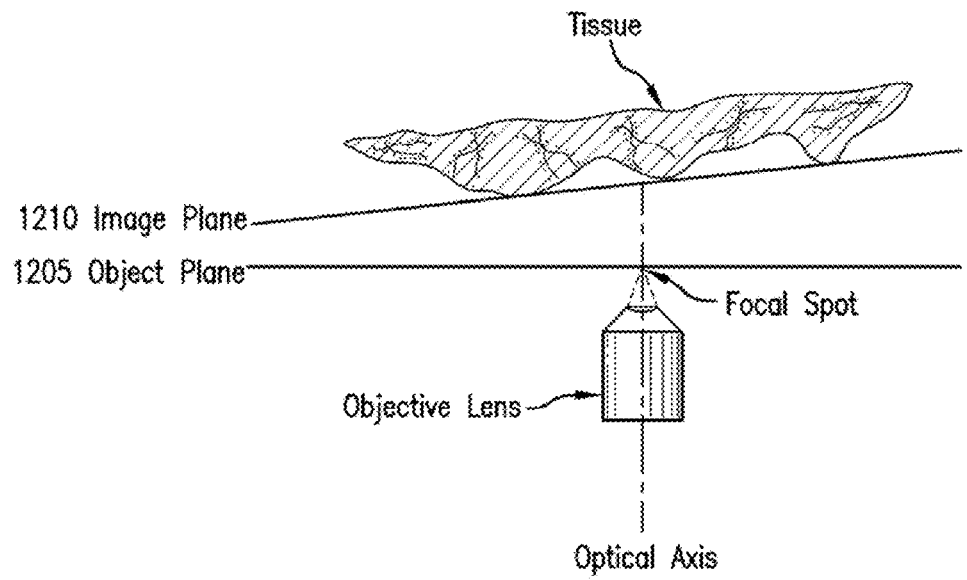
FIG. 12A is a side view of a possible result when the tissue is not flattened according to an exemplary embodiment of the present disclosure.
Figure 12B:
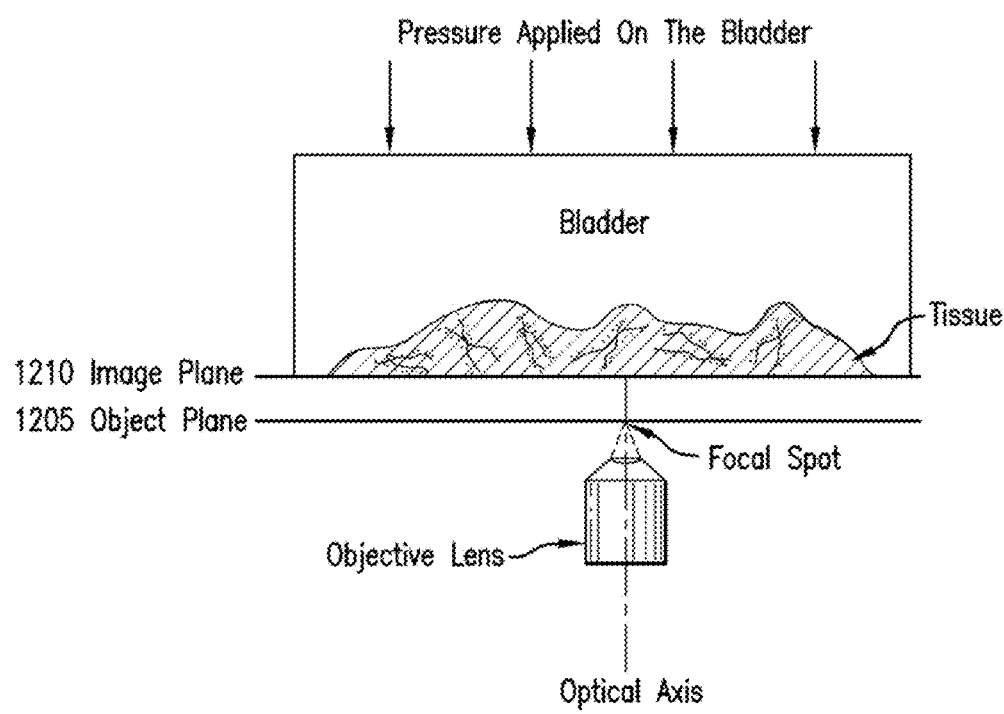
FIG. 12B is a side view of a possible result when the tissue is flattened using one or more exemplary devices according to the present disclosure according to an exemplary embodiment of the present disclosure.

In order to image a large area of the tissue with nuclear and cellular level resolution, the tissue can be scanned in a two-dimensional ("2D") "object plane" (e.g., a plane that can be approximately perpendicular to an optical axis of an objective lens) in the microscope. However, surgically excised, and biopsied, tissue can have a 3D topography with varying shape and size. Thus, it can be preferable that the tissue, especially the surface to be imaged, be flattened into a 2D plane that can conform to the object plane of the microscope, as shown in FIGS. 12A and 12B.

To that end, an exemplary embodiment of the tissue-mounting device according to the present disclosure can be provided to perform such exemplary procedure, as shown in FIGS. 1-4.

Figure 17:
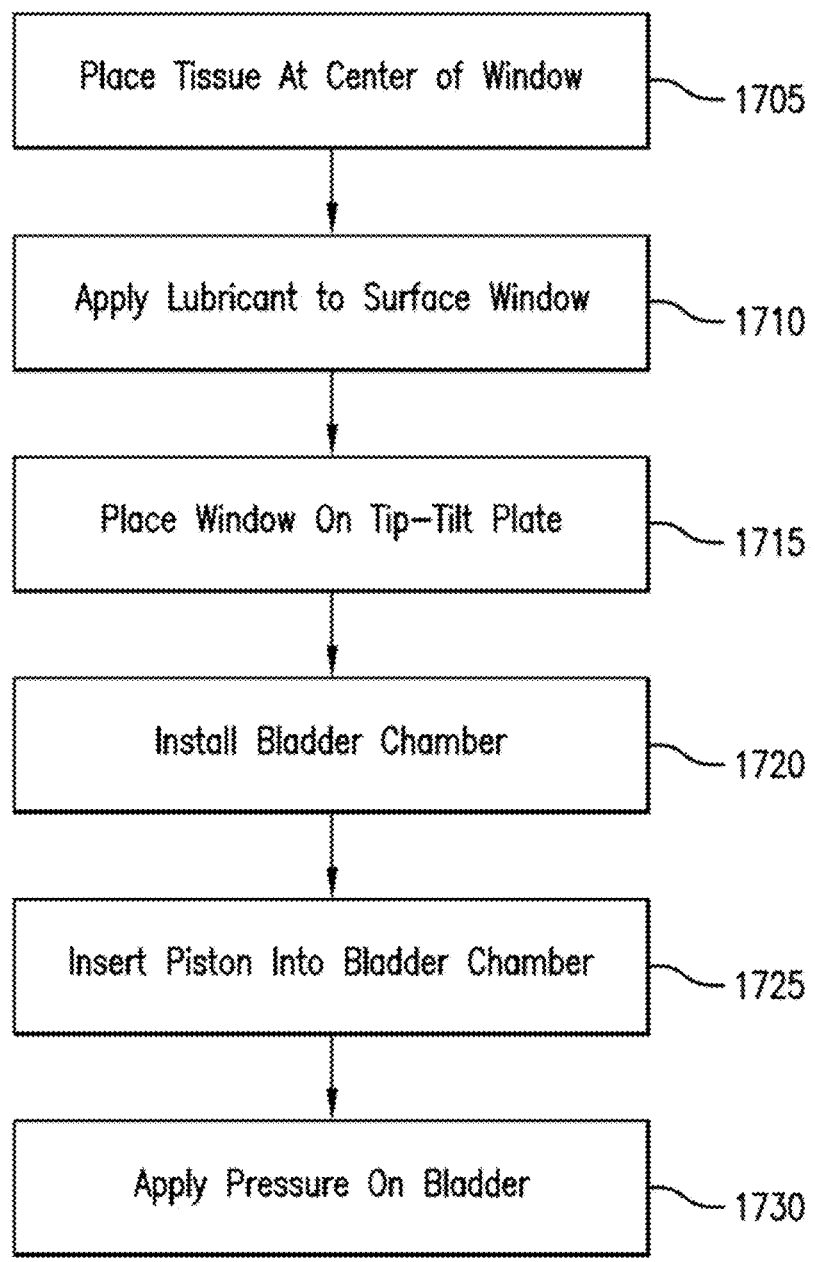
FIG. 17 is an exemplary flow diagram for flattening the exemplary tissue according to an exemplary embodiment of the present disclosure.

In particular, FIG. 1 illustrates a side cross-sectional view of an exemplary embodiment of the tissue-mounting device 100, with no force applied to a bladder 125, which can perform an exemplary procedure shown in FIG. 17. To flatten the desired (e.g., lower) surface of the tissue 105, a user can place the tissue 105 at the center of a window 110 of such exemplary tissue-mounting device 100 (e.g., procedure 1705 in FIG. 17). Then, the user can apply a surgical lubricant on the top surface of the window 110 (e.g., the surface where the tissue can be placed) around the sample, for example, approximately 5 mm outside a border of the sample (e.g., procedure 1710 in FIG. 17). Then, the window 110 can be placed on a tip-tilt plate 115 (e.g., procedure 1715 in FIG. 17) followed by installation of a polycarbonate bladder-chamber 120 on the tip-tilt plate 115 (e.g., procedure 1720 in FIG. 17). The exemplary tissue-mounting device 100 for fresh tissue 105 shown in FIG. 1 can have no force applied to the bladder 125. Under this nominal condition, the tissue surface (e.g., a lower surface of tissue 105), which can be imaged, may not be flattened on to the object plane.

Figure 2:
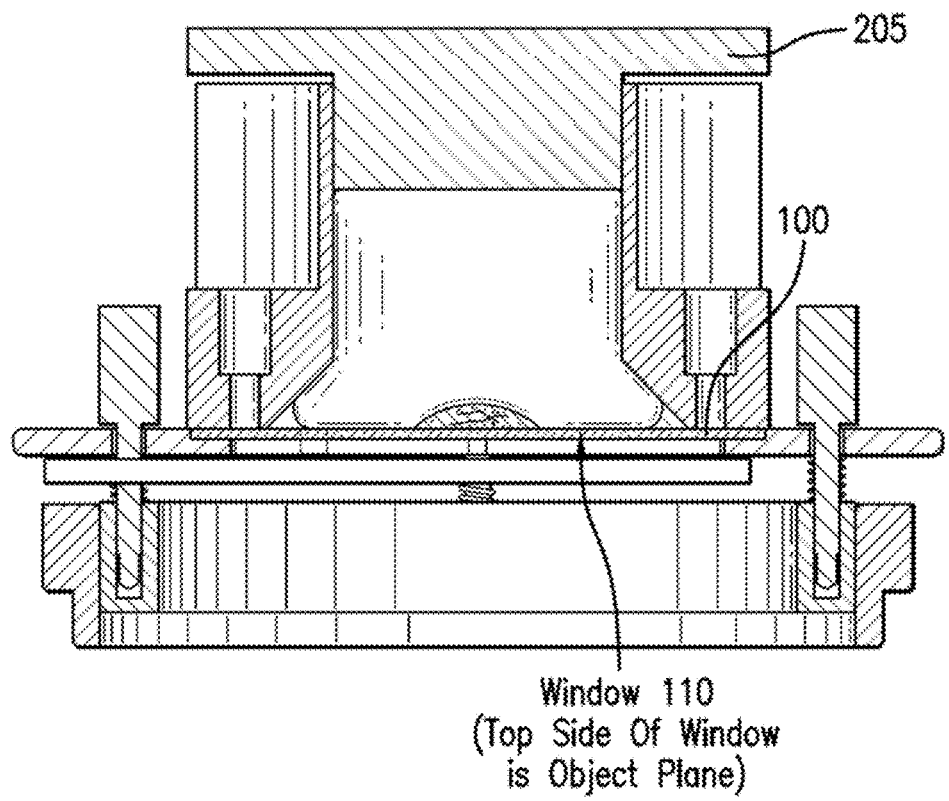
FIG. 2 is a side cross-sectional view of the exemplary tissue-mounting device of FIG. 1 with an inserted piston, during operation thereof according to an exemplary embodiment of the present disclosure.
Figure 4:
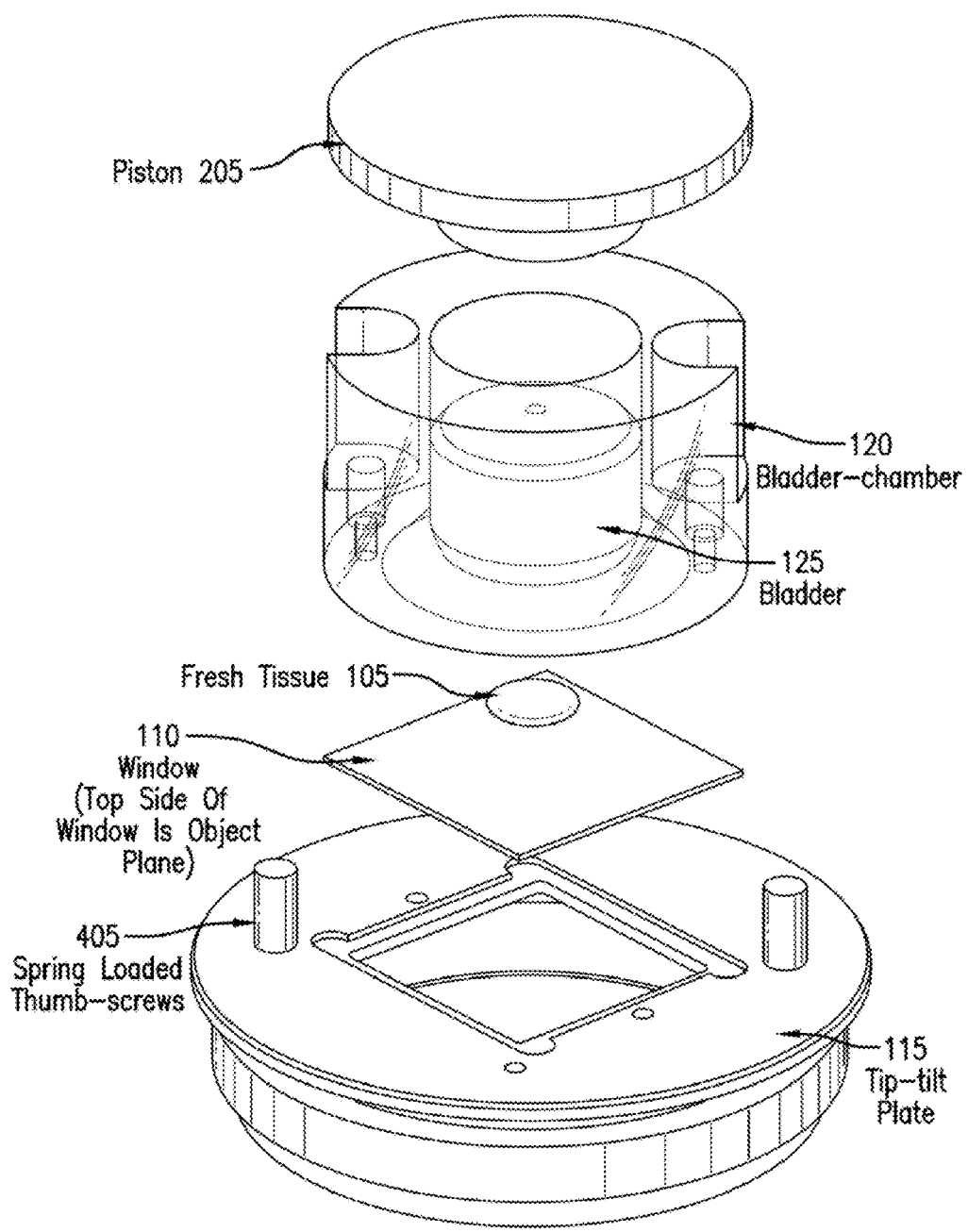
FIG. 4 is a perspective isometric (e.g., 3D) view of the exemplary tissue-mounting device of FIG. 1, with separate exemplary components illustrated therein according to an exemplary embodiment of the present disclosure.

FIG. 2 shows a side cross-sectional view of the exemplary tissue-mounting device 100 of FIG. 1 with an inserted piston 205, during operation thereof. In particular, as shown in FIG. 4, which illustrates a perspective isometric (e.g., 3D) view of the exemplary tissue-mounting device 100 of FIG. 1, with separate exemplary components illustrated therein, a polycarbonate piston 205 can be inserted into the bladder-chamber 120 of the tissue-mounting device 100 of FIG. 1 (e.g., procedure 1725 in FIG. 17), and pressed down gently to apply pressure on the bladder 125 (e.g., procedure 1730 in FIG. 17). This operation and force can flatten a lower surface of the tissue 105 against the window 110, and thus provide the tissue 105 into a desired 2D plane. The exemplary system/apparatus, which can be used to facilitate such flattening of the tissue, is illustrated in FIG. 4, which can facilitate the use of a microscope to analyze the flattened surface of the tissue.

Figure 3:
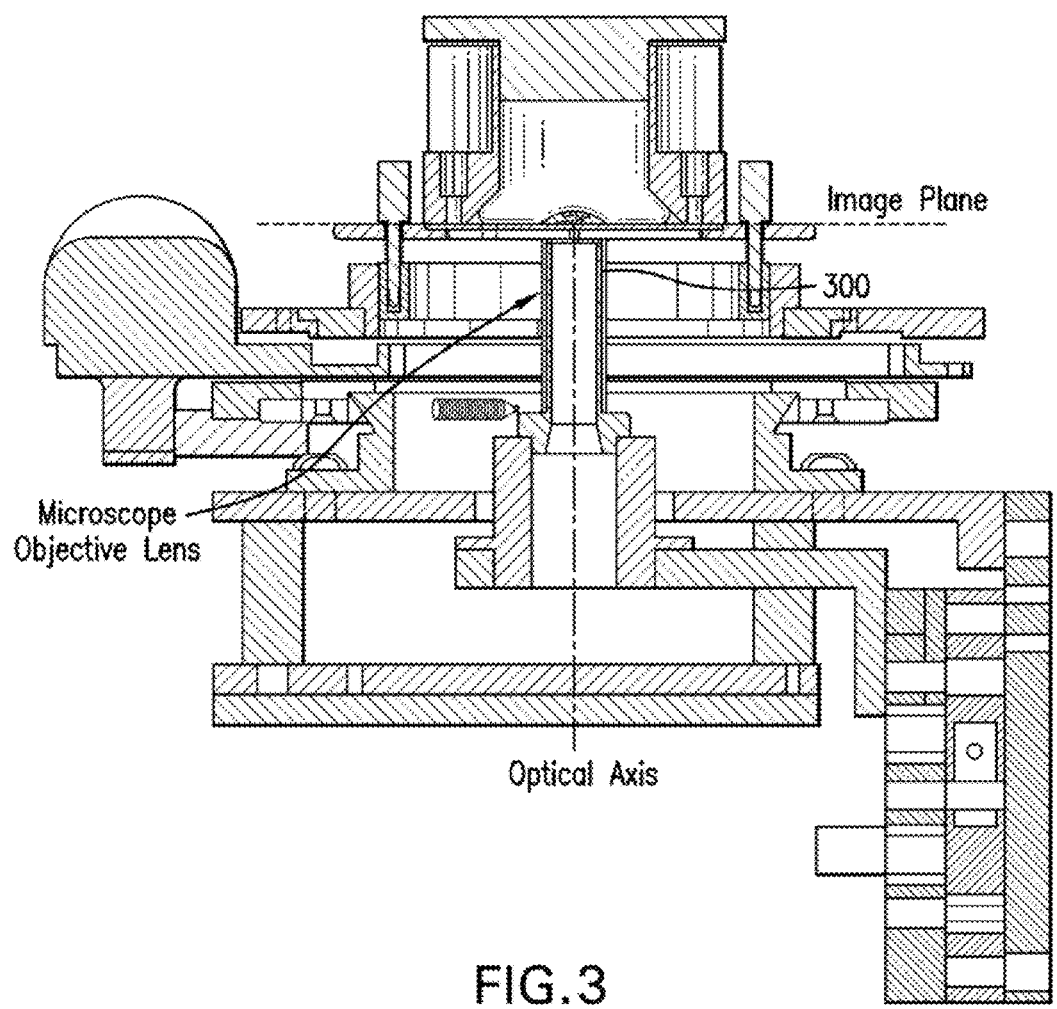
FIG. 3 is a side cross-sectional view of the exemplary tissue-mounting device of FIG. 1 installed in an exemplary microscope according to an exemplary embodiment of the present disclosure.

According to an exemplary embodiment of the present disclosure, position and orientation on a 2D plane in terms of tip and tilt, relative to the optical axis of the microscope, can be provided as shown in FIG. 3, which illustrates a side cross-sectional view of the exemplary tissue-mounting device 100 of FIG. 1 installed in a microscope 300, which can be adjusted with spring-loaded thumbscrews 405 shown in FIG. 4. This can facilitate an exemplary adjustment of the window 110 so that it can be parallel to the "object plane" of the microscope. Such exemplary system and method, according to an exemplary embodiment of the present disclosure can facilitate a desired surface of the tissue 105 to conform to the object plane of the microscope 300, to facilitate accurate and repeatable imaging and mosaicing over large areas. The exemplary embodiment and implementation of the mounting device can be robust to facilitate a repeatable operation during extended periods of time. Thus, the use of such fresh tissue mounting devices in confocal mosaicing microscopy, can enable rapid pathology at the bedside in diverse settings (e.g., for detection of residual cancer margins to guide surgery in surgical settings, and for screening/diagnosis of cancers to guide the examination of biopsies in clinical settings).

Figure 5:
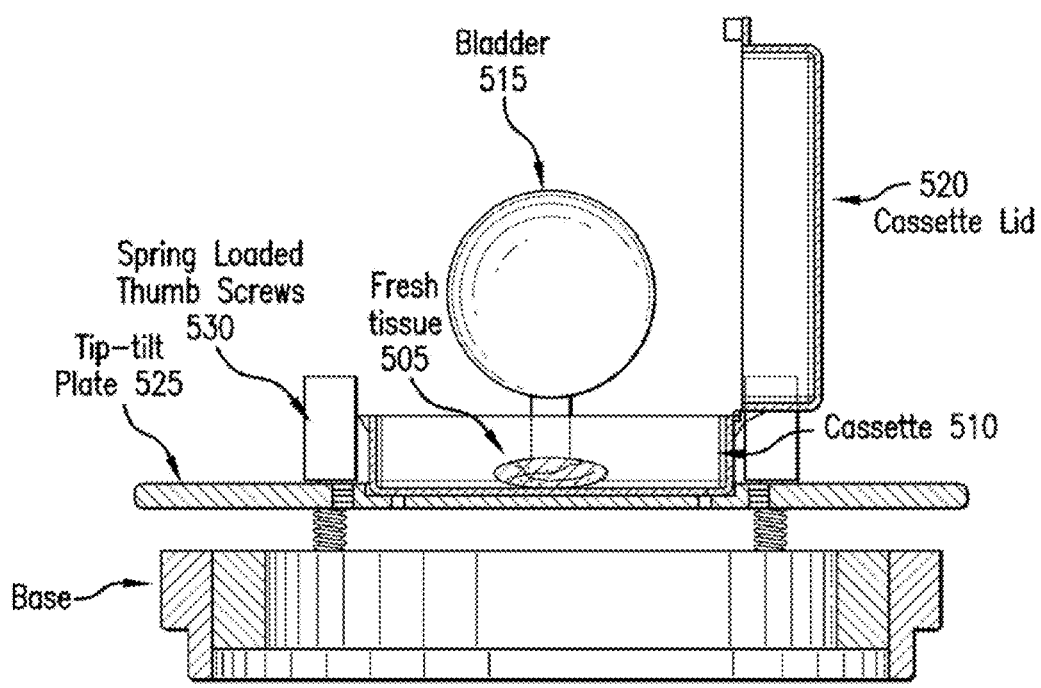
FIG. 5 is a side cross-sectional view of another exemplary embodiment of the exemplary tissue-mounting device for fresh tissue, with no force applied to the bladder according to a second exemplary embodiment of the present disclosure.
Figure 6:
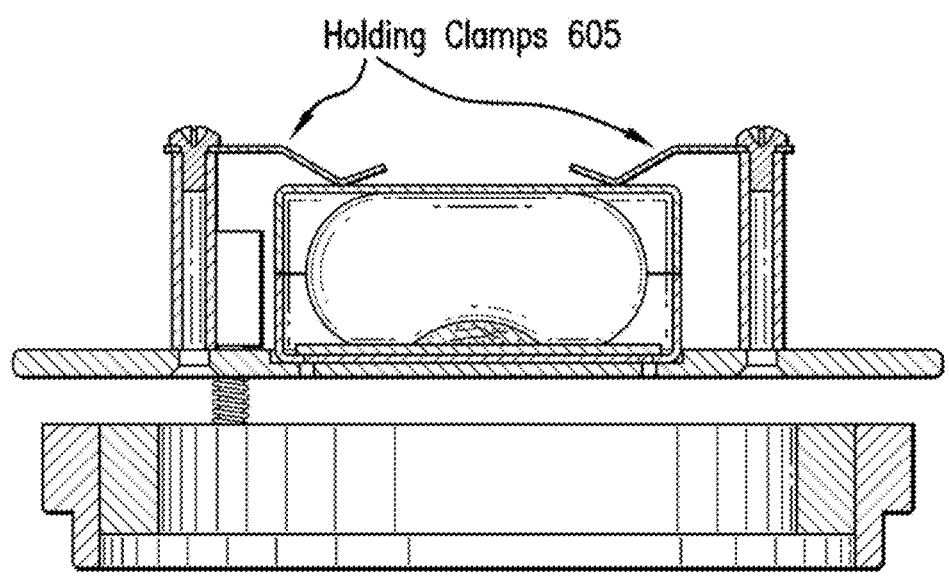
FIG. 6 is a side cross-sectional view of the exemplary tissue-mounting device of FIG. 5, with the exemplary cassette closed, during operation thereof according to an exemplary embodiment of the present disclosure.
Figure 18:
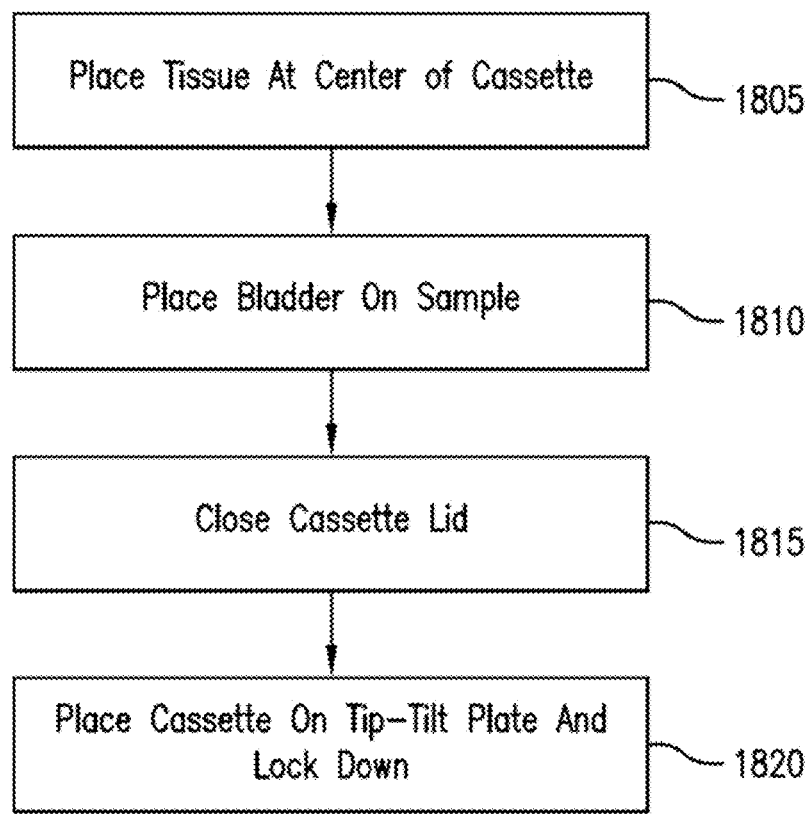
FIG. 18 is an exemplary flow diagram for flattening the exemplary tissue according to another exemplary embodiment of the present disclosure.

The exemplary flattening procedure illustrated in FIG. 18 can also be accomplished with another mounting device according to a further exemplary embodiment of the present disclosure, as illustrated in FIGS. 5-9. Thus, for example, as an initial step for the exemplary procedure to flatten the desired (e.g., lower) surface of the tissue 505, the user can place the tissue 505 at a center of the cassette 510 (e.g., procedure 1805 of FIG. 18), followed by placing the bladder 515 on the sample (e.g., procedure 1810 of FIG. 18), which is shown in FIG. 5. Such placement can also be done automatically by an automatic device, such as, for example, a robotic device, etc. Then, the user and/or the automatic device can close the cassette lid 520 (e.g., procedure 1815 of FIG. 18). Such exemplary closure of the lid 520 can apply pressure on the bladder 515 which can flatten the lower surface of the tissue 505 against the bottom surface of the cassette 510 into the desired 2D plane, as shown in FIG. 6. Then, as also illustrated in FIG. 6, the cassette 510 can be placed on the tip-tilt plate 525, and locked down with the holding clamps 605 (e.g., procedure 1020 of FIG. 18).

Figure 7:
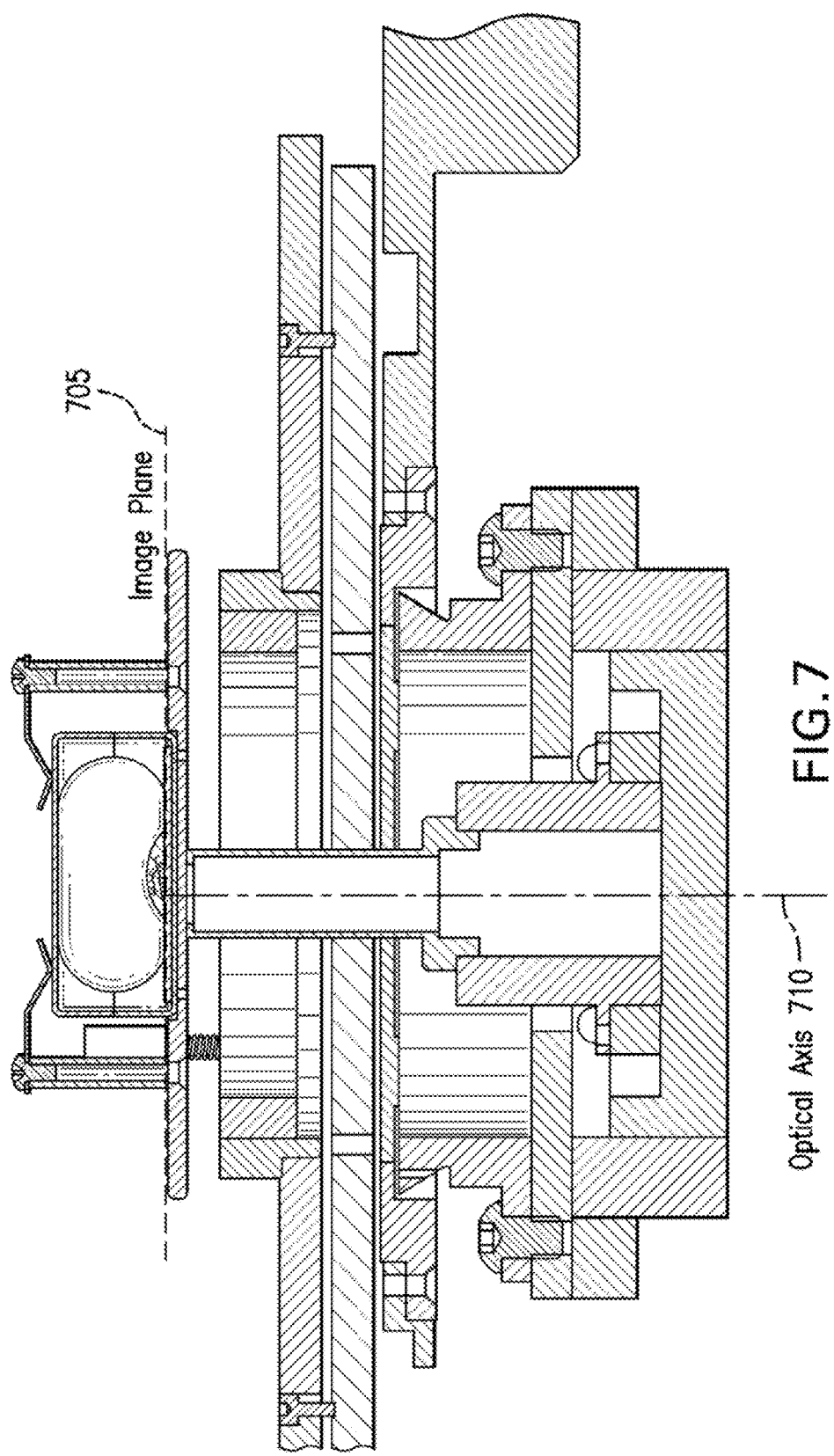
FIG. 7 is a side cross-sectional view of the exemplary tissue-mounting device of FIG. 5 installed in an exemplary microscope according to an exemplary embodiment of the present disclosure.

The 2D plane's position and orientation in terms of tip and tilt, relative to the optical axis of the microscope, can be adjusted with spring-loaded thumbscrews 530. This can facilitate an adjustment of the window so that it can be parallel to the object plane or the image plane 705, or approximately perpendicular to the optical axis of the microscope 710, as shown in FIG. 7.

Figure 8:
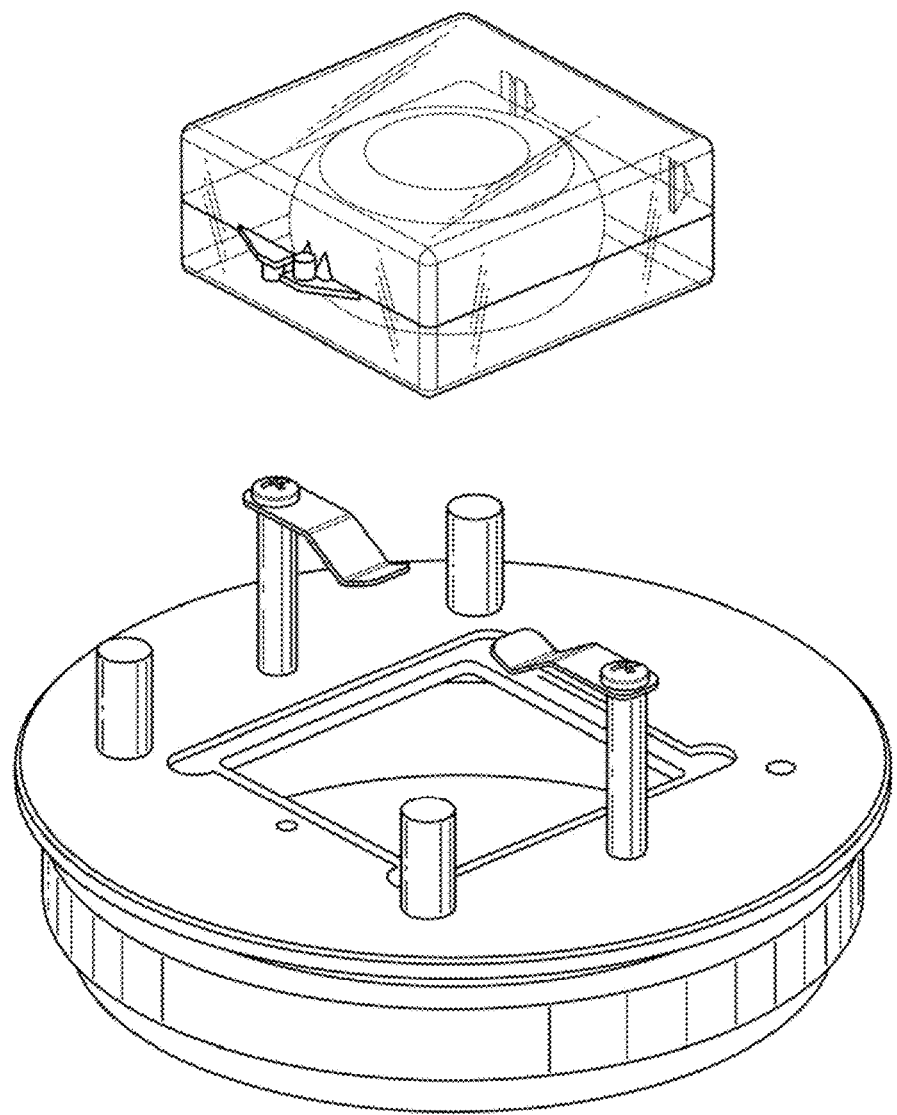
FIG. 8 is a perspective isometric (e.g., 3D) view of the exemplary tissue-mounting device of FIG. 5, with separate exemplary components illustrated therein according to an exemplary embodiment of the present disclosure.
Figure 9:
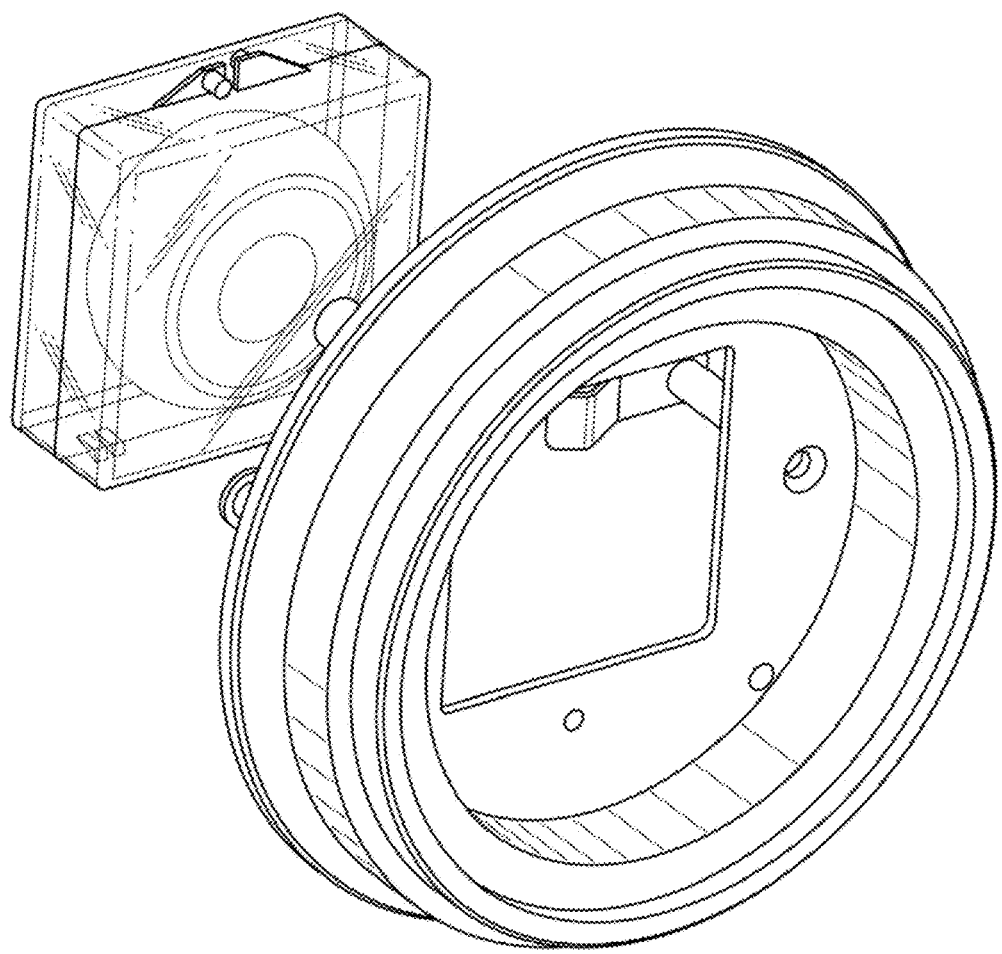
FIG. 9 is another perspective isometric (e.g., 3D) view of the exemplary tissue-mounting device of FIG. 5, with further separate exemplary components illustrated therein according to an exemplary embodiment of the present disclosure.

FIG. 8 is a perspective isometric (e.g., 3D) view of the exemplary tissue-mounting device of FIG. 5, with separate exemplary components illustrated therein. FIG. 9 provides another perspective isometric (e.g., 3D) view of the exemplary tissue-mounting device of FIG. 5, with such separate exemplary components illustrated therein.

Figure 10:
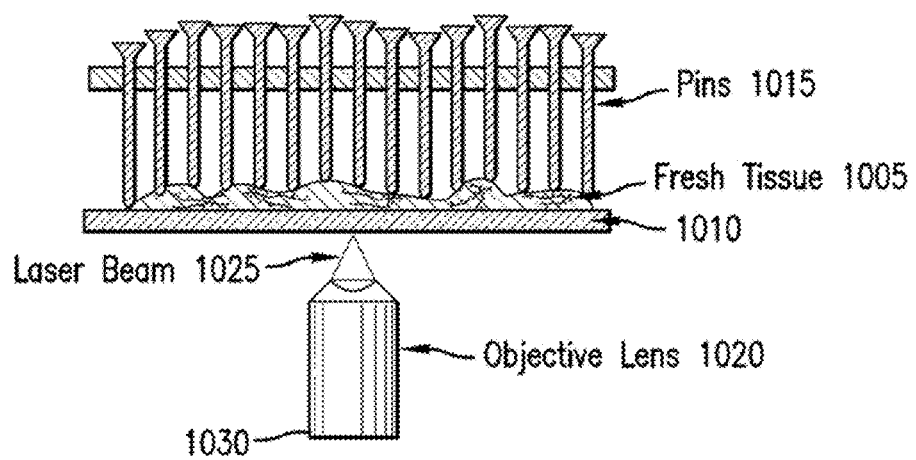
FIG. 10 is a side cross-sectional view of another exemplary tissue-mounting device for fresh tissue using a plurality of exemplary pins according to a third exemplary embodiment of the present disclosure.
Figure 19:
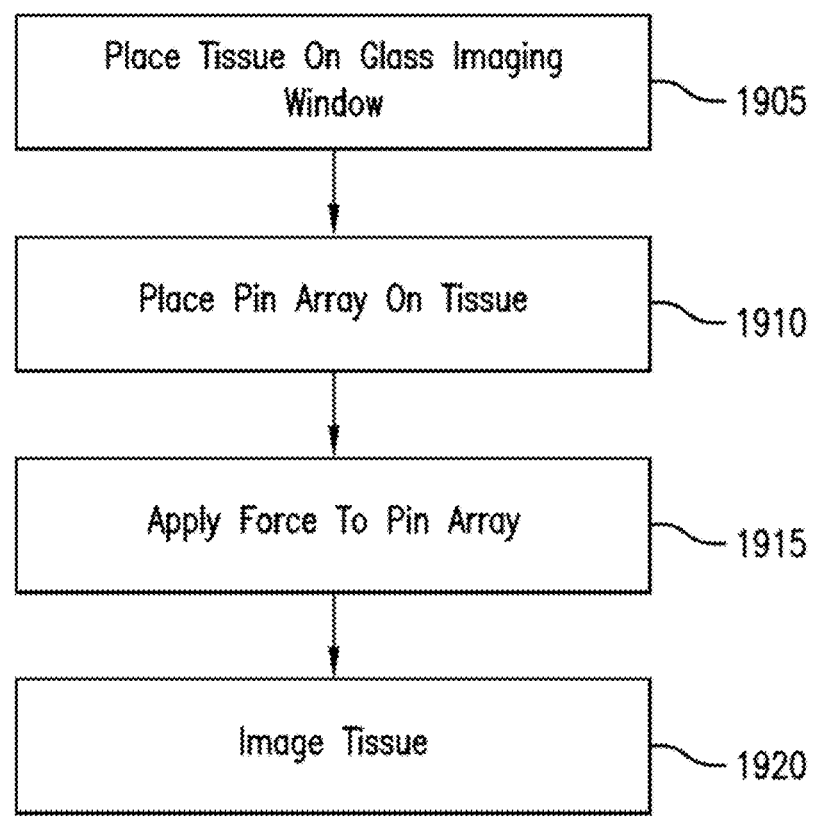
FIG. 19 is an exemplary flow diagram for flattening the exemplary tissue according to the third exemplary embodiment of the present disclosure.

The exemplary flattening procedure illustrated in FIG. 19 can also be accomplished with another mounting device according to a further exemplary embodiment of the present disclosure, as illustrated in FIG. 10. To flatten the desired (e.g., lower) surface, the user can place the fresh tissue 1005 on the glass imaging window 1010 (e.g., procedure 1905 of FIG. 19) and then placing the micro-pin array 1015 on the tissue 1005 (e.g., procedure 1910 of FIG. 19). Then, the user can apply a force on the pin array 1015 to flatten the lower surface of the tissue 1005 against the top surface of the imaging window 1010 into the desired 2D plane (e.g., procedure 1915 of FIG. 19). An imaging device 1030, which can include an objective lens 1020 and a laser beam 1025, can be used to image to fresh tissue 1005 (e.g., procedure 1920 of FIG. 19).

Figure 11:
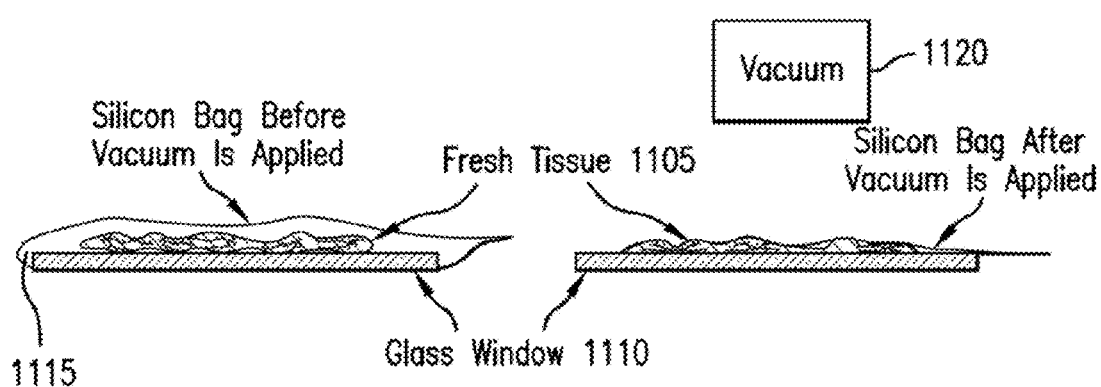
FIG. 11 is a side cross-sectional view of still another tissue-mounting device for fresh tissue using an exemplary silicon bag and an exemplary vacuum according to a fourth exemplary embodiment of the present disclosure.
Figure 20:
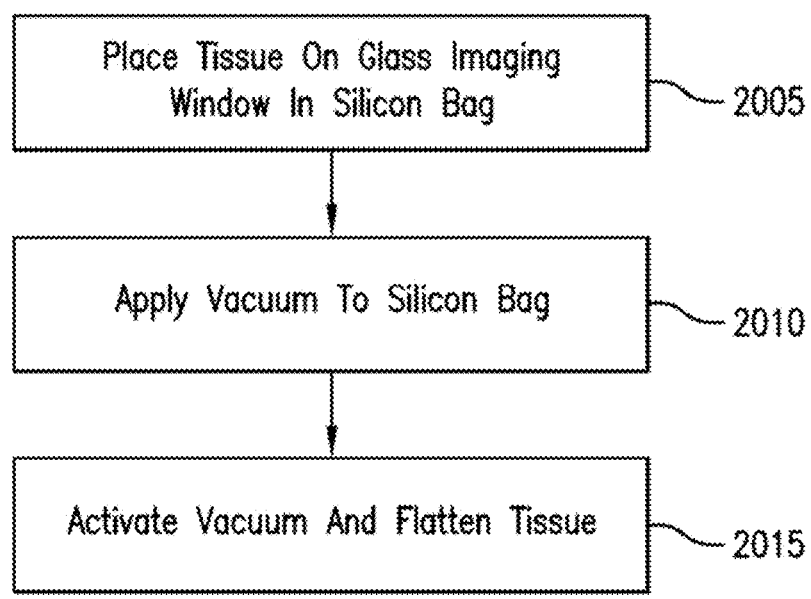
FIG. 20 is an exemplary flow diagram for flattening the exemplary tissue according to the fourth exemplary embodiment of the present disclosure.

The exemplary flattening procedure illustrated in FIG. 20 can also be accomplished with another mounting device according to a further exemplary embodiment of the present disclosure, as illustrated in FIG. 11. To flatten the desired (e.g., lower) surface the user can place the fresh tissue 1105 on the imaging window 1110 followed by placing the tissue/glass window in a bag (e.g., a thin silicon bag) 1115 (e.g., procedure 2005 of FIG. 20). Then, the user can apply a vacuum 1120 to the silicon bag 1115 (e.g., procedure 2010 of FIG. 20). This can apply atmospheric pressure, flattening the tissue 1105 against the top surface of the imaging window 110 into the desired 2D plane (e.g., procedure 2015 of FIG. 20).

FIG. 12A shows a side view of an exemplary illustration of a result of the tissue that may not be flattened, and thus, the object plane 1205 can likely not be parallel to the image plane 1210, and the optical axis may not be orthogonal to the image plane. FIG. 12B provides a side view of a possible result when the tissue can be flattened using one or more exemplary devices according to the present disclosure, thus making the object plane parallel to the image plane and the optical axis orthogonal to the image plane.

Tissue fixturing can be utilized when acquiring large number of images for mosaicing. Indeed, the exemplary desired tissue surface (e.g., to be imaged) can preferably be flattened, and positioned and oriented so as to be held approximately parallel to the microscope objective lens' object (e.g., focal) plane. Thus, when the tissue can be translated in, for example, two dimensions, the surface can remain at least approximately in the lens' focal plane. If the tissue surface can be tilted, then the lens' focal plane (e.g., imaging) can either "sink into" or "lift off" the tissue surface.

Figure 13A:
FIGS. 13A-16 are exemplary images of an exemplary embodiments of the exemplary tissue-mounting device in various stages of an exemplary operation according to an exemplary embodiment of the present disclosure.
Figure 13B:
Figure 13C:
Figure 13D:
Figure 13E:
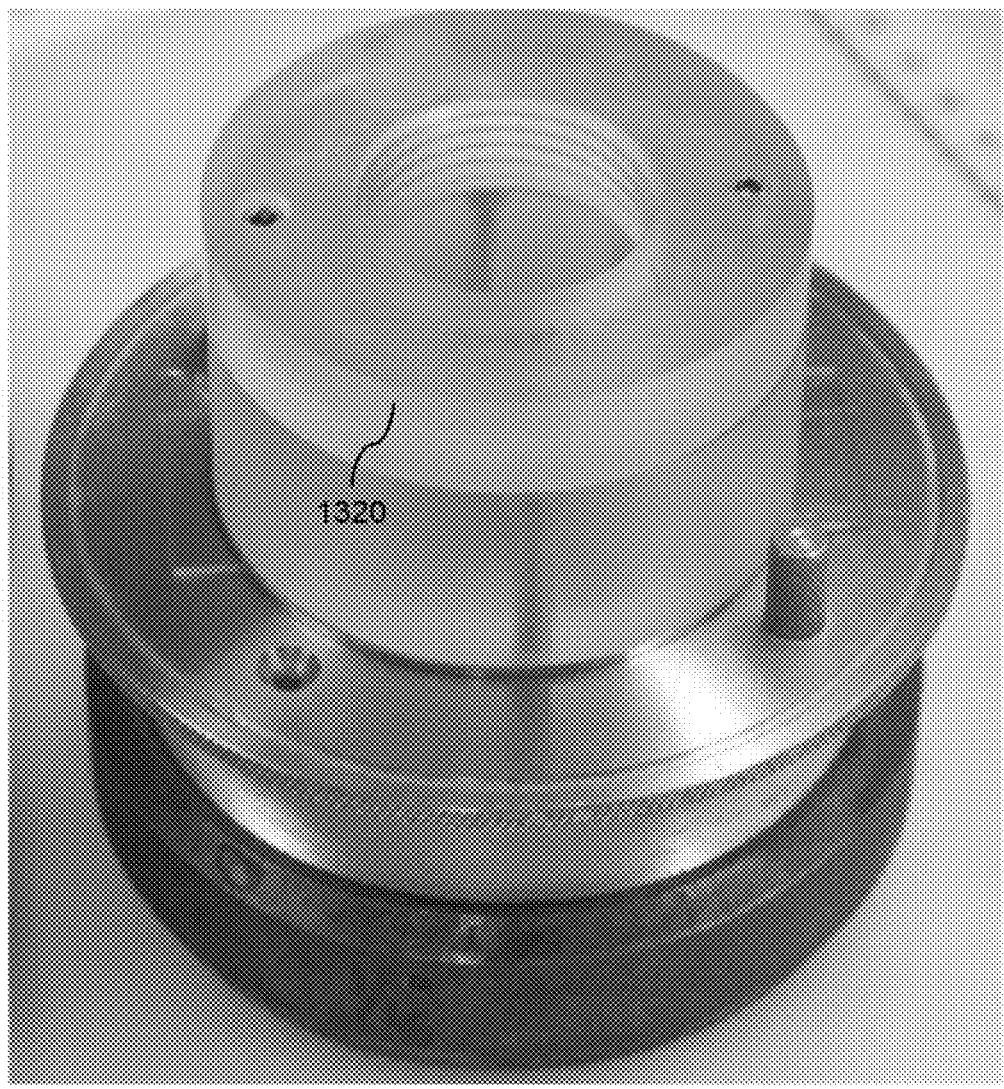
Figure 13F:
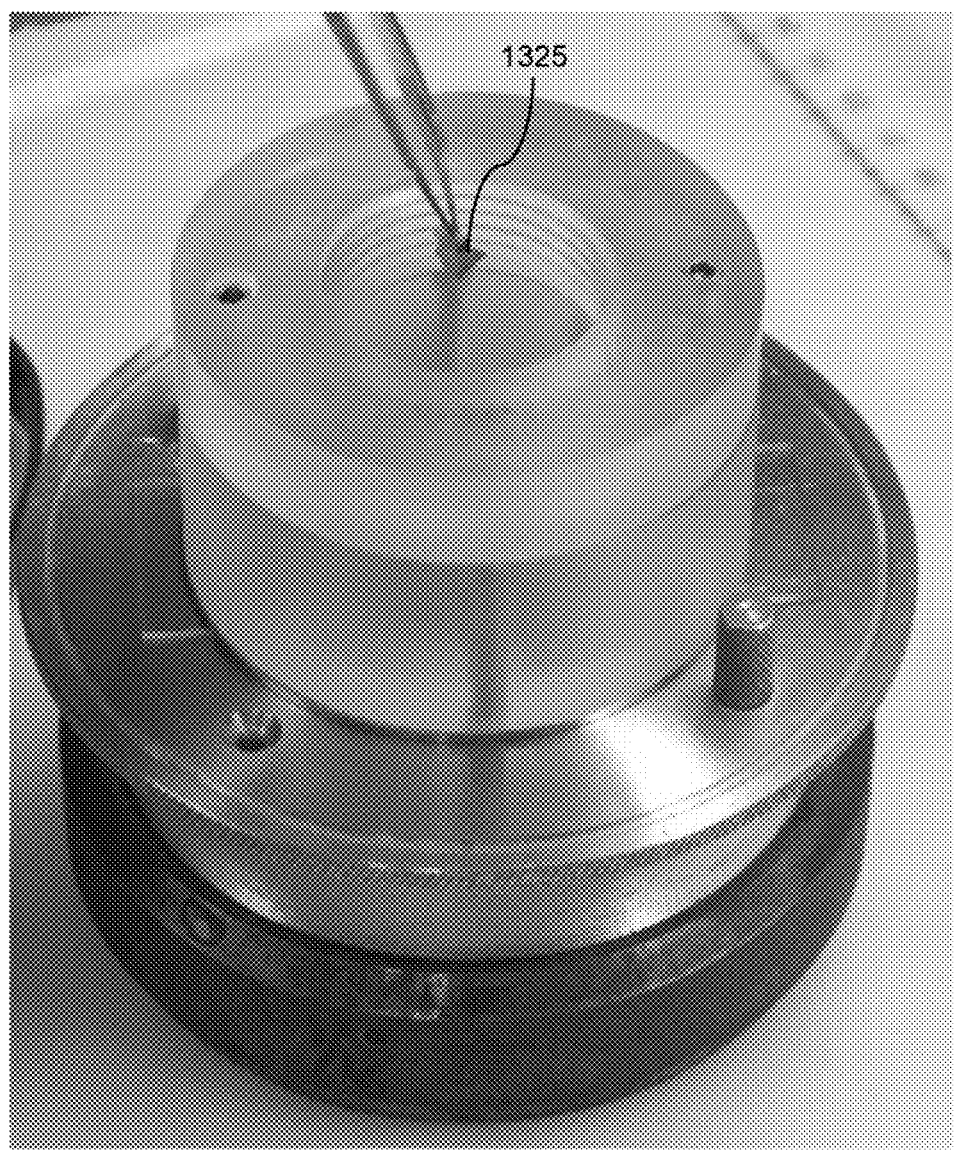
Figure 14:
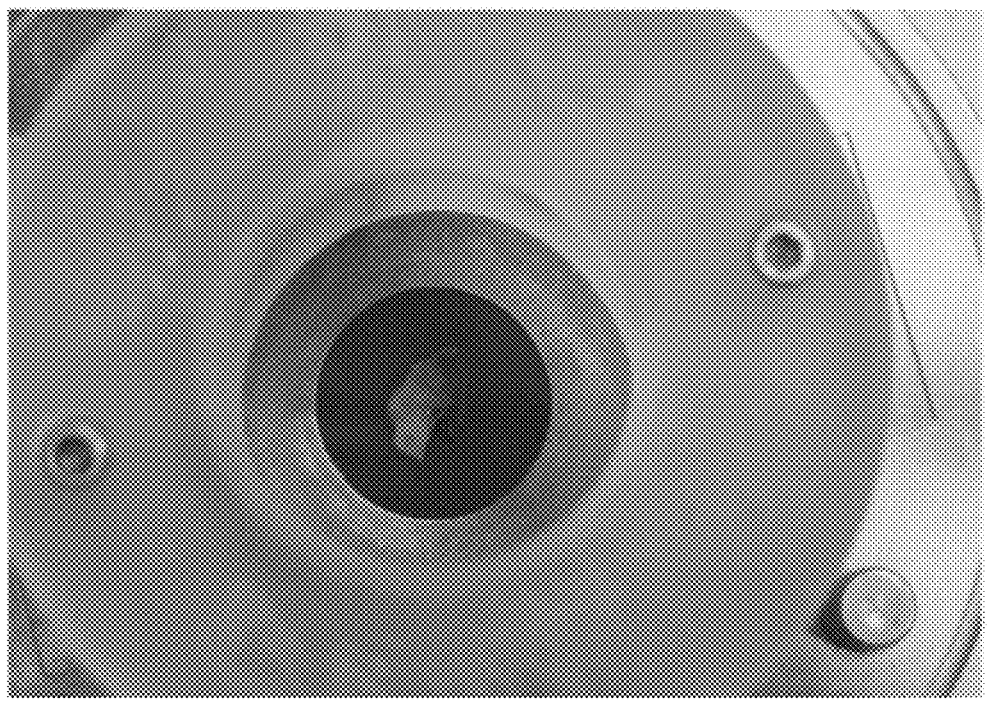
Figure 15A:
Figure 15B:
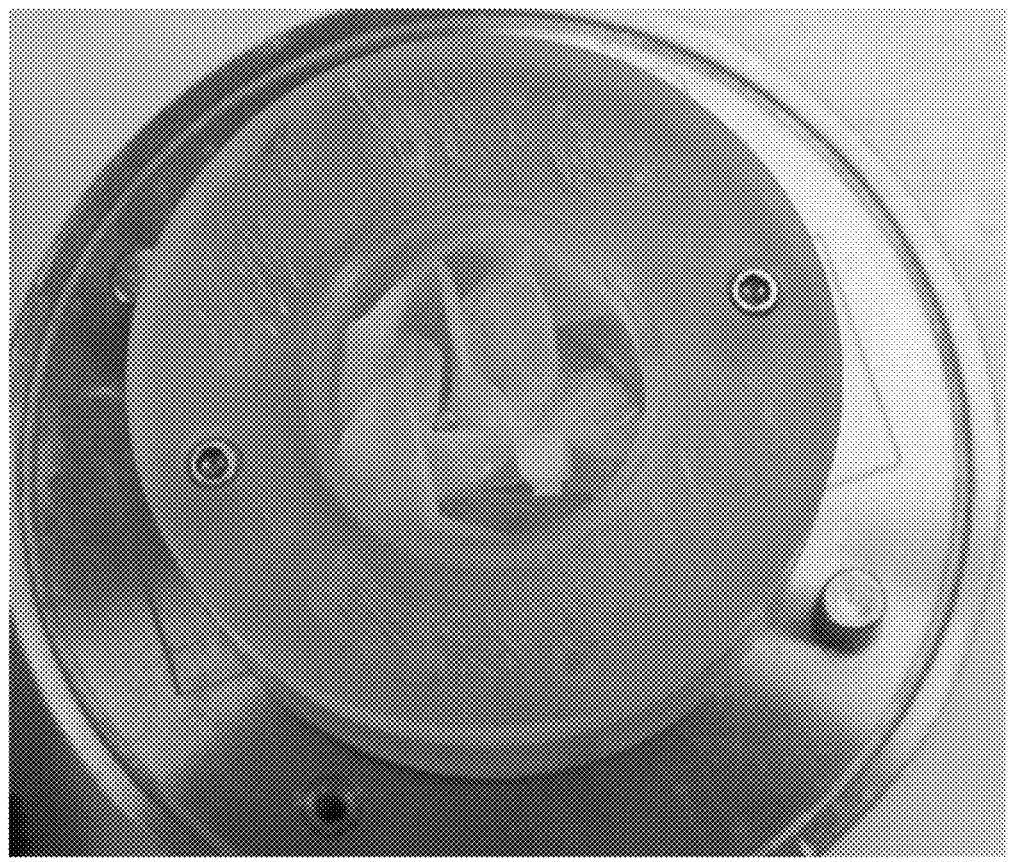
Figure 15C:
Figure 15D:
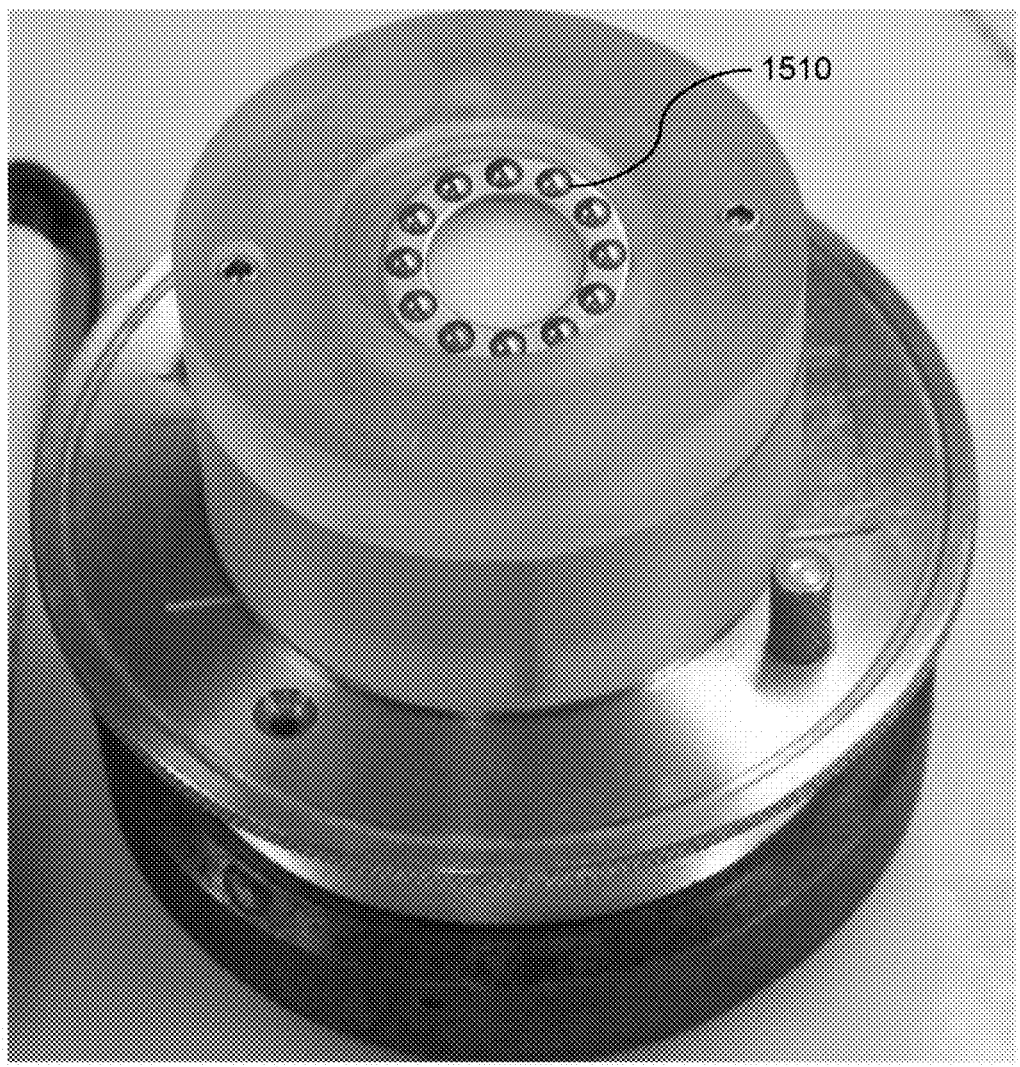
Figure 15E:
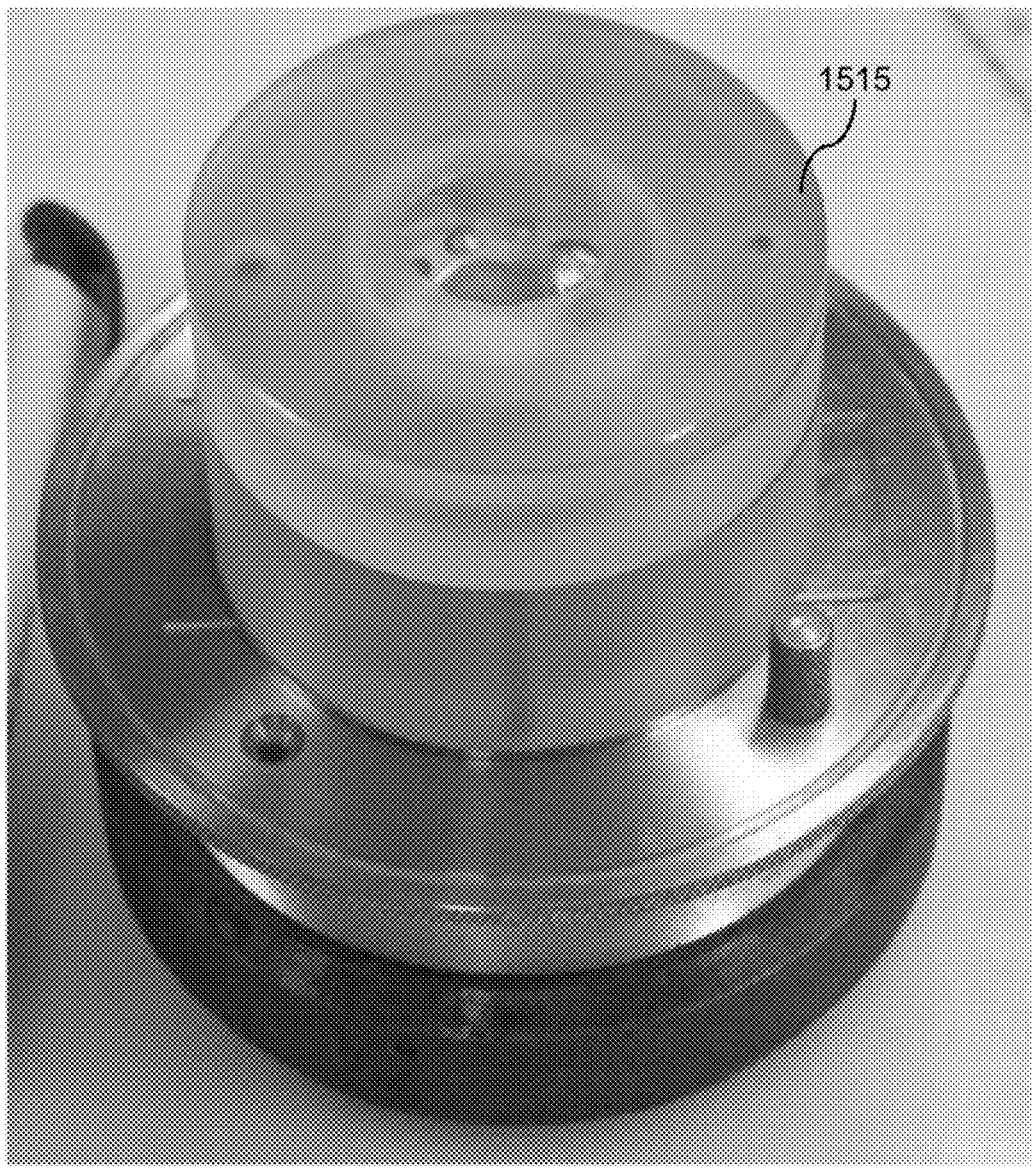
Figure 16:
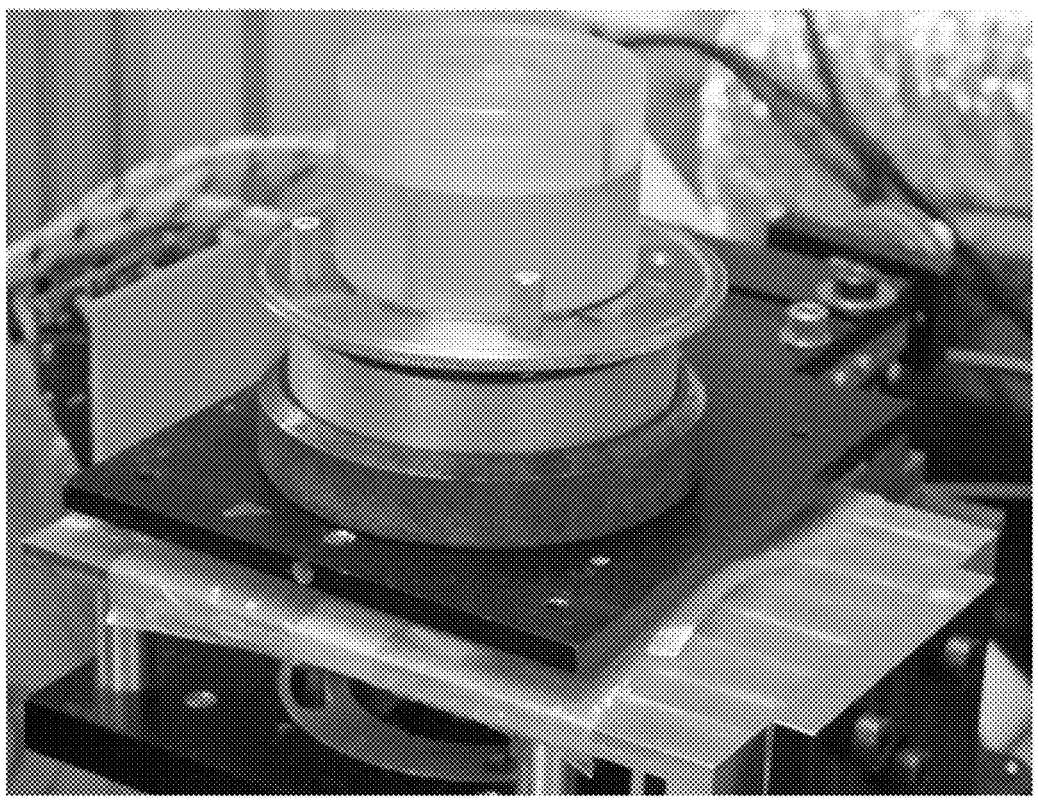

FIGS. 13A-16 show various illustrations of exemplary embodiments of the exemplary tissue-mounting devices in various stages of an exemplary operation. For example, FIG. 13A illustrates the exemplary tissue mounting device before an exemplary sample is placed thereon. FIG. 13B illustrates the exemplary tissue mounting device having an exemplary slide/window 1305 placed thereon. FIG. 13C illustrates the exemplary tissue mounting device having an exemplary plate 1310 placed on the exemplary slide/window 1305. FIG. 13D has an exemplary bladder chamber 1315 placed on the exemplary plate 1310. FIG. 13E illustrates the exemplary tissue mounting device having an exemplary piston holder 1320 placed on the exemplary bladder holder 1315. FIGS. 13F and 14 illustrate the exemplary tissue mounting device having an exemplary tissue sample 1325 placed inside of the exemplary bladder chamber 1315. FIGS. 15A-15C illustrate the exemplary tissue mounting device having an exemplary bladder 1305 placed inside of the exemplary bladder chamber 1315. FIG. 15D illustrates the exemplary tissue mounting device having a ball bearing ring 1510 placed inside of the bladder chamber 1315. FIG. 15E illustrates the exemplary tissue mounting device having a cover 1515 placed thereon. FIG. 16 illustrates the exemplary tissue mounting device being used to image an exemplary tissue sample 1325.

The foregoing merely illustrates the principles of the disclosure. Various modifications and alterations to the described embodiments will be apparent to those skilled in the art in view or the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced can be incorporated herein by reference in their entireties.

What is claimed is:

1. An apparatus for facilitating an analysis of at least one sample, comprising:
   at least one structural first arrangement having a substantially flat surface, which is configured to receive the at least one sample thereon, wherein the at least one structural first arrangement includes a window; and
   at least one force applying second arrangement which is configured to apply a first force on at least one portion of the at least one sample such that at least one surface of the at least one sample is flattened against the substantially flat surface of the at least one first arrangement,
   wherein the at least one second arrangement includes at least one structural third arrangement configured to contact the at least one portion, and at least one force applying fourth arrangement configured to apply a second force on the at least one third arrangement which causes the first force to be applied to the at least one portion.

2. The apparatus according to claim 1, wherein the at least one second arrangement is configured to apply the first force to an area of the at least one portion that is located on a further surface that is approximately opposite to the at least one surface.

3. The apparatus according to claim 1, wherein the at least one third arrangement includes at least one of (i) at least one inflatable arrangement or (ii) a plurality of pins.

4. The apparatus according to claim 3, wherein the at least one fourth arrangement includes at least one of (i) at least one piston or (ii) at least one cassette lid.

5. The apparatus according to claim 1, further comprising at least one optical arrangement configured to image the at least one sample through the window.

6. The apparatus according to claim 1, wherein the at least one third arrangement includes at least one flexible tissue holding arrangement and the at least one fourth arrangement includes at least one vacuum arrangement.

7. The apparatus according to claim 6, wherein the at least one flexible tissue holding arrangement includes at least one silicon bag.

8. The apparatus according to claim 1, further comprising at least one securing arrangement which is configured to at least one of directly or indirectly secure the at least one sample in a position to maintain the at least one surface in a flat manner against the at least one section.

9. The apparatus according to claim 1, further comprising at least one computer arrangement which is configured to obtain data regarding at least one portion of the at least one sample from below the at least one flattened surface.

10. The apparatus according to claim 9, wherein the at least one computer arrangement includes a microscope arrangement.

11. The apparatus according to claim 9, wherein the data includes image information regarding the at least one portion of the at least one sample.

12. A method for facilitating an analysis of at least one sample, comprising:
   providing at least one structural first arrangement having a substantially flat surface so as to receive the at least one sample thereon, wherein the at least one structural first arrangement includes a window;
   providing the at least one sample on the at least one first arrangement;
   providing (i) at least one force applying second arrangement which includes at least one structural third arrangement configured to contact the at least one portion, and (ii) at least one force applying fourth arrangement configured to apply a first force on the at least one third arrangement; and
   causing a second force to be applied on at least one portion of the at least one sample, based on the first force, such that at least one surface of the at least one sample is flattened against the substantially flat surface of the at least one first arrangement.

13. The method according to claim 12, wherein the at least one third arrangement includes at least one of (i) at least one inflatable arrangement or (ii) a plurality of pins.

14. The method according to claim 13, wherein the at least one third arrangement further includes at least one inflatable arrangement holder and the at least one fourth arrangement includes at least one piston.

15. The method of claim 14, further comprising inflating the at least one inflatable arrangement and screwing the at least one piston into the at least one inflatable arrangement holder to cause the at least one inflatable arrangement to apply the second force to the at least one sample.

16. The method according to claim 13, wherein the at least one fourth arrangement includes at least one cassette lid.

17. A method for facilitating an analysis of at least one sample, comprising:
   providing at least one structural first arrangement having a substantially flat surface so as to receive the at least one sample thereon;
   providing the at least one sample on the at least one first arrangement;
   providing (i) at least one force applying second arrangement which includes at least one structural third arrangement configured to contact the at least one portion, and (ii) at least one force applying fourth arrangement configured to apply a first force on the at least one third arrangement, wherein the at least one third arrangement includes at least one of (i) at least one inflatable arrangement or (ii) a plurality of pins, and wherein the at least one fourth arrangement includes at least one cassette lid;
   causing a second force to be applied on at least one portion of the at least one sample, based on the first force, such that at least one surface of the at least one sample is flattened against the substantially flat surface of the at least one first arrangement; and
   inflating the at least one inflatable arrangement and closing the at least one cassette lid to cause the at least one inflatable arrangement to apply the second force to the at least one sample.

18. The method according to claim 12, further comprising imaging the at least one sample through the window.

19. The method according to claim 12, wherein the at least one third arrangement includes at least one flexible tissue holding arrangement and the at least one fourth arrangement includes at least one vacuum arrangement.

20. The method of claim 19, further comprising placing the at least one sample in the at least one flexible tissue holding arrangement, and vacuuming air from the at least one flexible tissue holding arrangement using the at least one vacuum to apply the second force.

21. The method according to claim 19, wherein the at least one flexible tissue holding arrangement includes at least one silicon bag.

22. An apparatus for facilitating an analysis of at least one sample, comprising:
   at least one structural first arrangement having a window which is configured to receive the at least one sample thereon;
   at least one force applying second arrangement which is configured to apply a first force on at least one portion of the at least one sample such that at least one surface of the at least one sample is flattened against at least one section of the at least one first arrangement, and
   at least one optical arrangement configured to image the at least one sample through the window,
   wherein the at least one second arrangement includes at least one structural third arrangement configured to contact the at least one portion, and at least one force applying fourth arrangement configured to apply a second force on the at least one third arrangement which causes the first force to be applied to the at least one portion.

23. A method for facilitating an analysis of at least one sample, comprising:
   providing at least one structural first arrangement so as to receive the at least one sample thereon;
   providing the at least one sample on the at least one first arrangement;
   providing (i) at least one force applying second arrangement which includes at least one structural third arrangement configured to contact the at least one portion, and (ii) at least one force applying fourth arrangement configured to apply a first force on the at least one third arrangement, wherein the at least one structural third arrangement includes at least one inflatable arrangement and the at least one fourth arrangement includes at least one cassette lid; and
   inflating the at least one inflatable arrangement and closing the at least one cassette lid to cause the at least one inflatable arrangement to apply a second force to at least one portion of the at least one sample, based on the first force, such that at least one surface of the at least one sample is flattened against at least one section of the at least one first arrangement.

* * * * *